United States Patent
Phivilay et al.

(10) Patent No.: US 12,312,302 B2
(45) Date of Patent: May 27, 2025

(54) TRANSALKYLATION OF ALKYLATED PHENOLS

(71) Applicants: UOP LLC, Des Plaines, IL (US); CHINA PETROLEUM & CHEMICAL CORPORATION, Beijing (CN)

(72) Inventors: Somphonh Peter Phivilay, Brookshire, TX (US); Neelesh Rane, Des Plaines, IL (US); Liwei Guo, Katy, TX (US); Zhenhua Zhou, Katy, TX (US)

(73) Assignees: UOP LLC, Des Plaines, IL (US); China Petroleum & Chemical Corporation, Beijing (CN)

( * ) Notice: Subject to any disclaimer, the term of this patent is extended or adjusted under 35 U.S.C. 154(b) by 41 days.

(21) Appl. No.: 18/040,995

(22) PCT Filed: Sep. 30, 2020

(86) PCT No.: PCT/US2020/053547
§ 371 (c)(1),
(2) Date: Feb. 8, 2023

(87) PCT Pub. No.: WO2022/071942
PCT Pub. Date: Apr. 7, 2022

(65) Prior Publication Data
US 2023/0286889 A1    Sep. 14, 2023

(51) Int. Cl.
C07C 6/12    (2006.01)
B01J 29/80    (2006.01)
(Continued)

(52) U.S. Cl.
CPC ............... C07C 37/50 (2013.01); B01J 29/80 (2013.01); C07C 6/123 (2013.01); B01J 29/40 (2013.01); B01J 29/7007 (2013.01)

(58) Field of Classification Search
CPC ............. B01J 29/80; C07C 37/50; C07C 6/12
See application file for complete search history.

(56) References Cited

U.S. PATENT DOCUMENTS 3,091,646 A    5/1963    Leston
3,933,927 A    1/1976    Goddard
(Continued)

FOREIGN PATENT DOCUMENTS

CN    1098028 A    2/1995
CN    1228073 A    9/1999
(Continued)

OTHER PUBLICATIONS

International Search Report from corresponding PCT application No. PCT/US2020/053547 mailed Jun. 17, 2021.
(Continued)

Primary Examiner — Sharon Pregler
(74) Attorney, Agent, or Firm — Greer, Burns & Crain, Ltd.

(57) ABSTRACT

Transalkylation processes using catalysts comprising three dimensional 12 membered ring zeolites with a combination of small and large pores are described. These catalysts have increased conversion of alkylphenols to phenol, cresols, and alkylbenzenes from coal-derived liquid streams compared to catalysts consisting of HZSM-5 zeolite.

18 Claims, 5 Drawing Sheets

(51) Int. Cl.
    *C07C 37/50*     (2006.01)
    *B01J 29/40*     (2006.01)
    *B01J 29/70*     (2006.01)

(56) References Cited

U.S. PATENT DOCUMENTS

| | | |
|---|---|---|
| 4,230,896 A | 10/1980 | Daly |
| 4,283,571 A | 8/1981 | Keim et al. |
| 4,503,269 A | 3/1985 | Engel et al. |
| 4,605,790 A | 8/1986 | Wojtkowski |
| 6,297,417 B1 | 10/2001 | Samson et al. |
| 6,936,744 B1 | 8/2005 | Cheng et al. |
| 9,067,853 B2 | 6/2015 | Frey et al. |
| 10,087,376 B2 | 10/2018 | Yanagawa et al. |
| 2020/0031741 A1 | 1/2020 | Zhou et al. |
| 2020/0061593 A1 | 2/2020 | Kamakoti et al. |
| 2020/0385322 A1 | 12/2020 | Loveless et al. |
| 2021/0139399 A1* | 5/2021 | Zhang .................. C07C 37/48 |

FOREIGN PATENT DOCUMENTS

| | | | |
|---|---|---|---|
| CN | 1386113 A | | 12/2002 |
| CN | 1428319 A | | 7/2003 |
| CN | 102863311 A | | 1/2013 |
| CN | 106479379 A | * | 3/2017 |
| CN | 110214131 A | | 3/2020 |
| GB | 748269 | | 4/1956 |
| GB | 1232027 | | 5/1971 |
| WO | 2011090121 A1 | | 7/2011 |
| WO | 2019103726 A1 | | 5/2019 |
| WO | 2019177458 A1 | | 9/2019 |
| WO | 2019177961 A1 | | 9/2019 |
| WO | 2020162876 A1 | | 8/2020 |
| WO | 2020162877 A1 | | 8/2020 |

OTHER PUBLICATIONS

Written Opinion from corresponding PCT application No. PCT/US2020/053547 mailed Jun. 17, 2021.

Xiaoming Huang et al., Selective Production of Biobased Phenol from Lignocellulose-Derived Alkylmethoxyphenols, ACS Catal., 2018, 8, 11184-11190.

Takuya Yoshikawa et al., Conversion of alkylphenol to phenol via transalkylation using zeolite catalysts, Catalysis Today 347 (2020) 110-114.

Yuhe Liao et al, Shape selectivity vapor-phase conversion of lignin-derived 4-ethylphenol to phenol and ethylene over acidic aluminosilicates: Impact of acid properties and pore constraint, Applied Catalysis B: Environmental 234 (2018) 117-129.

Takuya Yoshikawa et al., Conversion of alkylphenol to phenol via transalkylation using zeolite catalysts, Catalysis Today (2018), https://doi.org/10.1016/j.cattod.2018.08.009.

Danny Verboekend et al., Alkylphenols to phenol and olefins by zeolite catalysis: a pathway to valorize raw and fossilized lignocellulose, Green Chem., 2015, 18, 297.

International Preliminary Report on Patentability from corresponding PCT application No. PCT/US2020/053547 issued Mar. 28, 2023.

Office Action from corresponding Japanese application No. 2023-513614, dated Jul. 8, 2024.

Moeketsi, K., Transalkylation of Higher Methylphenols with Phenol to Produce Cresols and Xylenols, May 2007.

Chinese Office Action from corresponding Chinese application No. CN202080103554.8, dated Jan. 17, 2025.

Shanghai Federation of Economic Organizations, New Approaches and Technologies for Energy Conservation and Emission Reduction.

* cited by examiner

TRANSALKYLATION OF ALKYLATED PHENOLS

This application is a U.S. National Phase under 35 U.S.C. § 371 of International Application No. PCT/US2020/053547 filed Sep. 30, 2020, which is incorporated herein by reference in its entirety.

BACKGROUND OF THE INVENTION

Low and medium temperature coal tar contains an abundant of valuable oxygenate compounds such as phenol, cresols, and xylenols along with less desirable longer-chain alkylphenols in the feed.

Direct dealkylation can be employed to convert the alkylphenols; however, there are a number of problems associated with the process. When direct dealkylation is done without a catalyst, the process temperature is in the range of 700 to 900° C. This can lead to the dealkylation of the phenols through thermal cracking at the high process temperature. It is quite energy intensive because of the high process temperature. In addition, it is normally not selective due to the loss of the hydroxyl group. Catalytic dealkylation can be done at much milder conditions. At temperatures from 300 to 400° C., ethylphenol and propylphenol can be dealkylated to produce phenol and ethylene/propylene on a ZSM-5 zeolite. However, water usually has to be co-fed to prevent severe catalyst deactivation. In addition, cresols dealkylation is relatively difficult, and phenol selectivity can be a concern.

Therefore, there is a need for improved methods of converting alkylphenols in coal tar feeds to obtain phenol and xylenes. Transalkylation of the alkylphenols with a co-reactant (e.g., a co-reactant such as benzene or toluene) can help to prevent the loss of the hydroxyl group due to less severe process temperatures and will produce alkylbenzenes as co-products which are more valuable compared to ethylene/propylene produced from dealkylation.

DESCRIPTION OF THE INVENTION

Coal-derived feed streams, such as low temperature coal tar, medium temperature coal tar, high temperature coal tar, cresylic acid, or a crude phenolic mixture contain phenol, alkylphenols (methylphenols (cresols), ethylphenols, dimethylphenols(xylenols), propylphenols, butylphenols, methylethylphenols, etc.), as well as heavier alkylphenols (such as indanols and napthols). Coal tar is derived from the process of dry distillation and gasification of coal and is classified based on the temperature used for this process (400-600° C. (low temperature), 600-1000° C. (medium temperature), and >1000° C. (high temperature)). Cresylic acid is a generic term referring to combinations of phenol and alkylphenols, and it can be obtained from either coal or petroleum processing, for example. A crude phenolic mixture can be obtained by the processing of coal tar oils and the purification of phenol containing waste from coke ovens, low temperature carbonization, and hydrogenation plants, for example. The composition of the feed stream will vary depending on its source.

The undesirable longer-chain alkylphenols in the coal-derived feed streams can be separated into a coal-derived liquid stream and converted to valuable products including, but not limited to, phenol, cresols, and xylenes by transalkylation. The alkylphenols in the coal-derived liquid stream can be transalkylated with a co-reactant (e.g., a co-reactant, such as benzene and/or toluene) to transfer the longer-chain alkyl group (for example, ethyl, propyl, butyl, etc.) to obtain phenol and alkylbenzenes as the new products. The alkylbenzenes, for example, xylenes, ethylbenzene, and ethyltoluenes, are in demand for industrial processes and have higher value compared to toluene. In some cases, it has been determined that phenols with methyl groups, such as cresols, xylenols, and trimethylphenols, are not easily transalkylated with an aromatic compound so the valuable phenolics remain intact.

WO 2019177458 (WO '458) demonstrated that 4-propylphenol (model feed for biomass lignin-derived phenol) can be transalkylated with benzene using an HZSM-5 catalyst. Several other zeolites were tested (HMOR and HY) but were not as active as HZSM-5.

In "Conversion of alkylphenol to phenol via transalkylation using zeolite catalysts," Yoshikawa et al., Catalysis Today, (2018), https://dol.org/1-.1016/j.cattod.2-18.08.009, it was demonstrated that 4-propylphenol (a model feed for biomass lignin-derived phenol) can be transalkylated with benzene in a batch reactor over HBeta, HZSM-5 and HMOR zeolites. They found that HZSM-5 yielded a greater amount of transalkylation products (phenol and propylbenzenes) than HBeta or HMOR zeolites.

US 2020/0031741 describes a process and apparatus for cresol transalkylation with toluene and/or benzene to phenol and aromatics/alkylbenzenes in the presence of transalkylation catalysts (homogeneous or heterogeneous acid catalysts) from coal-derived liquids. It also describes xylenol transalkylation with benzene to make phenol and aromatics/alkylbenzenes in the presence of transalkylation catalysts.

However, the feeds in these references were limited (i.e., a single compound) and did not involve a broad range of alkylphenols. Low and medium temperature coal tar, cresylic acid, and a crude phenolic mixture are complex mixtures of alkylphenols, and contain a greater percentage of dimethylphenols (e.g., 3.0-34.5 wt %), methylethylphenols (e.g., 0-3.0 wt %) and ethylphenols (e.g., 2.0-38.5 wt %) than propylphenols (e.g., 0-1%). The methyl and ethyl groups of alkylphenols are much harder to remove than the propyl groups.

The coal-derived liquid stream from the coal-derived feed stream comprises a complex mixture of alkylphenols comprising one or more methylphenols (cresols), ethylphenols, dimethylphenols (xylenols), propylphenols, butylphenols, methylethylphenols, etc.), as well as heavier alkylphenols (such as indanols and napthols). It has been found that catalysts comprising three dimensional 12 membered ring zeolites with a combination of smaller and larger pores have increased conversion of these complex mixtures of alkylphenols to phenol, cresols, and alkylbenzenes compared to catalysts consisting of HZSM-5 zeolite.

One suitable zeolite comprising three dimensional 12 membered rings with a combination of smaller and larger pores is HBeta zeolite. Catalysts made with these zeolites have increased conversion of complex mixtures of alkylphenols as described above to phenol, cresols, and alkylbenzenes compared to catalysts consisting of HZSM-5 zeolite. The catalysts comprising HBeta zeolites are very stable in the transalkylation process, with less than about 5% decrease in conversion of alkylphenols to phenol, cresols, and alkylbenzenes over 25 hr. As a result, catalysts containing HBeta zeolites can be successfully used to convert low and medium temperature coal tar, cresylic acid, or a crude phenolic mixture to phenol, cresols, and aromatics, such as benzene and xylenes.

Any suitable HBeta zeolite can be used. HBeta zeolite is a three dimensional zeolite with 12 membered ring channels and a combination of large and small pores. The diameter of the larger pores are 6.6×6.7(Å), and the diameter of the small pores are 5.6×5.6 (Å) (www.iza-structure.org/databases/). The aluminum in the zeolite framework structure may be substituted, either partially or completely, by other metals including, but not limited to, Fe, Ga, B, Ti, Sn, Zr, and combinations thereof. The HBeta zeolite can have a silica/metal oxide molar ratio of 1-200, or 200 or below, or 150 or below, or 100 or below, or 80 or below, or 60 or below, or 50 or below, or 40 or below, or 30 or below, or 25 or below. When the metal oxide is alumina, this is commonly referred to as SAR (silica/alumina ($SiO_2/Al_2O_3$) ratio). When another metal is partially substituted for aluminum in the framework structure, the amount of metal oxide in the silica/metal oxide ratio is the total amount of metal oxide (i.e., the amount of alumina+the amount of other metal oxide). HBeta zeolites are available from many companies, including, but not limited to, Zeolyst International, Clariant Ltd, and TOSOH Corporation. Some properties of HBeta zeolites are compared to other common zeolites in Table 1.

Of the HBeta zeolites tested, the catalysts containing HBeta SAR 25 zeolites were found to be the best catalysts for transalkylation of ethylphenols and methylphenols with toluene and for the transalkylation of 2,6 xylenol with toluene.

The catalyst comprising HBeta zeolite has a product selectivity to phenol, cresols and alkylbenzenes is 70% or more, or 75% or more, or 80% or more, or 85% or more, or 90% or more, or 95% or more. The catalyst comprising HBeta zeolite has a conversion of 4-ethylphenol of 60% or more, or 65% or more, or 70% or more, or 75% or more, or 80% or more. The catalyst comprising HBeta zeolite has a conversion of 2,6-xylenol of 20% or more, or 30% or more, or 40% or more.

The catalyst comprising HBeta zeolite has a productivity to phenol, cresols, and alkylbenzenes of 500 g/Kg-catalyst/h or more, or 750 g/Kg-catalyst/h or more, or 1000 g/Kg-catalyst/h or more, or 1250 g/Kg-catalyst/h or more, or 1300 g/Kg-catalyst/h or more, or 1500 g/Kg-catalyst/h or more, or 1750 g/Kg-catalyst/h or more, or 2000 g/Kg-catalyst/h or more.

$$\text{Conversion (\%)} = \frac{(\text{Reactant Moles IN} - \text{Reactant Moles OUT})}{(\text{Reactant Moles IN})} \times 100$$

$$\text{Product Selectivity (mol \%)} = \frac{\text{Product (moles)}}{\text{All Carbon containing Products (moles)}} \times 100$$

$$\text{Productivity}\left(\frac{g}{kg \cdot hr}\right) = \frac{\text{Product Mass OUT} \left(\frac{g}{hr}\right)}{\text{Catalyst Amount (kg)}}$$

The catalyst composition can be modified to improve catalyst stability and selectivity to the desired products with minimal side reactions. For example, other zeolites (including, but not limited to, HZSM-5, HY, HMOR, HMCM-22, and others) can be mixed with HBeta to adjust the activity and product selectivity. Additionally, the catalyst composition could include promoters typically including, but not limited to, one or more of transition metals from Group IB to VIII, alkali metals from Group IA, alkaline earth metals from Group IIA, rare earth metals from Lanthanide series, metal oxides, metal sulfides, metal nitrides, metal phosphides, and combinations thereof. The catalyst can also be combined with a porous inorganic support material, such as alumina, silica, zirconia, titania, and combinations thereof.

The catalyst typically comprises about 50 wt % HBeta zeolite or more, or about 60 wt % or more, or about 70 wt % or more, or about 75 wt % or more, or about 80 wt % or more, or about 85 wt % or more, or about 90 wt % or more, or about 95 wt % or more, or about 50% to 100%, or about 50% to about 99%, or about 50% to about 97%, or about 50% to about 95%.

The catalyst may comprise less than about 40 wt % HZSM-5 catalyst, or less than about 35 wt %, or less than about 30 wt %, or less than about 25 wt %, or less than about 20 wt %, or less than about 15 wt %, or less than about 10 wt %, or less than about 5 wt %, or less than about 3 wt %, or less than about 1 wt %.

The catalyst can perform transalkylation of alkylphenols including methylphenols (cresols), ethylphenols, dimethylphenols (xylenols), propylphenols, butylphenols, methylethylphenols, and the like, including complex mixtures thereof, such as coal-derived liquid streams, efficiently and in a low-cost process.

The transalkylation process can be performed in any suitable reactor type, including but not limited to, fixed bed reactors, moving bed reactors, ebullated bed reactors, fluidized bed reactors, continuous catalyst regeneration (CCR) reactors, semi-regenerative reactors, batch reactors, continuous stirred tank (CSTR) reactors, and slurry bed reactors, or combinations thereof.

Any suitable transalkylation reaction conditions can be used. The transalkylation reaction conditions will depend on the particular reactor type use, as is known in the art. For example, with a fixed bed reactor, the transalkylation reaction conditions can include at least one of: a temperature in a range of about 50° C. to about 600° C.; a pressure in a range of about 0 to about 15 MPa; or a liquid weight hourly space velocity in a range of about 0.1 to about 30 $hr^{-1}$. Those of skill in the art can select the appropriate reaction conditions for the reactor being used.

One aspect of the invention is a process for transalkylation. In one embodiment, the process comprises: transalkylating a coal-derived liquid stream comprising alkylphenols in a transalkylation reaction zone under transalkylation conditions in the presence of a co-reactant and a transalkylation catalyst comprising a three dimensional 12 membered ring zeolite with a combination of small and large pores to produce a transalkylation effluent stream comprising one or more of phenol, cresols, and alkylbenzenes, the process having increased conversion of alkylphenols to phenol, cresols, and alkylbenzenes compared to a catalyst consisting of HZSM-5 zeolite.

In some embodiments, the zeolite comprises about 50 wt % HBeta or more.

In some embodiments, the silica/metal oxide molar ratio of the zeolite is 80 or below.

In some embodiments, the transalkylation catalyst further comprises about 40 wt % HZSM-5 zeolite or less.

In some embodiments, the transalkylation catalyst comprises about 50% or more HBeta zeolite and 1 to 40% HZSM-5 zeolite, and wherein the process has increased productivity to phenol or cresols or both compared to a transalkylation catalyst consisting of HZSM-5 zeolite.

In some embodiments, aluminum from the zeolite framework structure is substituted by at least one of Fe, Ga, B, Ti, Sn, Zr, and combinations thereof.

In some embodiments, the zeolite further comprises a promoter comprising one or more of: transition metals, alkali metals, alkaline earth metals and rare earth metals, metal oxides, metal sulfides, metal nitrides, metal phosphides, and combinations thereof.

In some embodiments, the catalyst further comprises a support comprising alumina, silica, zirconia, titania, or combinations thereof.

In some embodiments, the coal-derived liquid stream comprises a mixture of alkylphenols comprising two or more of: a methylphenol, an ethylphenol, a dimethylphenol, a butylphenol, a methylethylphenol, an indanol, and a naphthol, and optionally further comprising a propylphenol.

In some embodiments, the co-reactant may be a co-reactant such as benzene, toluene, or a combination thereof.

In some embodiments, transalkylating the coal-derived liquid stream takes place in the presence of hydrogen, nitrogen, or a combination thereof.

In some embodiments, the transalkylation reaction zone comprises a fixed bed reactor, a moving bed reactor, an ebullated bed reactor, a fluidized bed reactor, a continuous catalyst regeneration (CCR) reactor, a semi-regenerative reactor, a batch reactor, a continuous stirred tank (CSTR) reactor, a slurry reactor, or combinations thereof.

In some embodiments, productivity to phenol, cresols and alkylbenzenes is 1300 g/Kg-catalyst/h or more.

In some embodiments, selectivity to phenol, cresols and alkylbenzenes is about 70% or more.

In some embodiments, the coal-derived liquid stream comprises a low temperature coal tar stream, a medium temperature coal tar stream, a high temperature coal tar stream, a cresylic acid stream, or a crude phenolic mixture.

In some embodiments, the process further comprises: separating the transalkylation effluent into a phenol product stream comprising the phenol and an alkylbenzene stream comprising the alkylbenzenes.

In some embodiments, the process further comprises: separating the alkylbenzene stream into at least a recycle co-reactant stream such as one or more of benzene or toluene; and recycling the recycle co-reactant stream to the transalkylation zone and wherein the recycle stream comprises at least a part of the co-reactant.

In some embodiments, separating the alkylbenzene stream into at least a recycle co-reactant stream comprises separating the alkylbenzene stream into at least the recycle co-reactant stream and a mixed xylenes stream comprising para-xylene, ortho-xylene, and meta-xylene; and recovering one or more of para-xylene, ortho-xylene, or meta-xylene from the mixed xylenes stream.

In some embodiments, separating the transalkylation effluent into the product stream and the alkylbenzene stream comprises separating the transalkylation effluent into the phenol product stream, the alkylbenzene stream, and a cresol product stream comprising the cresols, and further comprises: recovering the cresol product stream.

In some embodiments, the transalkylation effluent stream further comprises unreacted alkylphenols, and wherein separating the transalkylation effluent into the product stream and the alkylbenzene stream comprises separating the transalkylation effluent into the phenol product stream, the alkylbenzene stream, and an unreacted alkylphenol stream comprising the unreacted alkylphenols, and further comprises: recycling the unreacted alkylphenol stream to the transalkylation reaction zone.

In some embodiments, the process further comprises: providing a coal-derived feed stream comprising phenol and the coal-derived liquid stream; separating the coal-derived feed stream into at least a phenol stream comprising phenol and the coal-derived liquid stream before transalkylating the coal-derived liquid stream; and recovering the phenol stream.

In some embodiments, the process further comprises: providing a coal-derived feed stream comprising phenol and the coal-derived liquid stream; separating the coal-derived feed stream into at least a phenol-cresol stream comprising phenol and cresols and the coal-derived liquid stream before transalkylating the coal-derived liquid stream; and recovering the phenol-cresol stream.

EXAMPLES

The following commercial catalysts were evaluated.

| Zeolite | Manufacture (Material Code) | Silica/Alumina Molar Ratio (SAR)* |
|---|---|---|
| HBeta | Clariant (HCZB25) | 25 |
| HBeta | Zeolyst (CP814C) | 38 |
| HBeta | Clariant (HCZB150) | 150 |
| HZSM-5 | Clariant (NH4CZP30) | 30 |
| HZSM-5 | Zeolyst (CBV8014) | 80 |
| HZSM-5 | Zeolyst (CBV28014) | 280 |
| HY | Zeolyst (CBV500) | 5.2 |
| HY | Zeolyst (CBV712) | 12 |
| HMOR | Zeolyst (CBV21A) | 38 |

*Provided by manufacturer.

Example 1

Several commercial zeolites were evaluated for the transalkylation of 4-ethylphenol (4-EP) with toluene to form phenol and ethyltoluenes.

The reaction conditions included using an isothermal fixed bed reactor set to a temperature of 400° C., a pressure of 1350 psig, a WHSV of 2.3 $h^{-1}$, 1.25 g catalyst, toluene:feed of 11 mol/mol, and $N_2$ feed rate of 25 mL/min. The catalyst was pretreated in $N_2$ and heated to 200° C. (3° C./min) and held at 200° C. for 2 h followed by heating to 450° C. (5° C./min) and held for 3 h before cooling down to 400° C.

Figure 1:
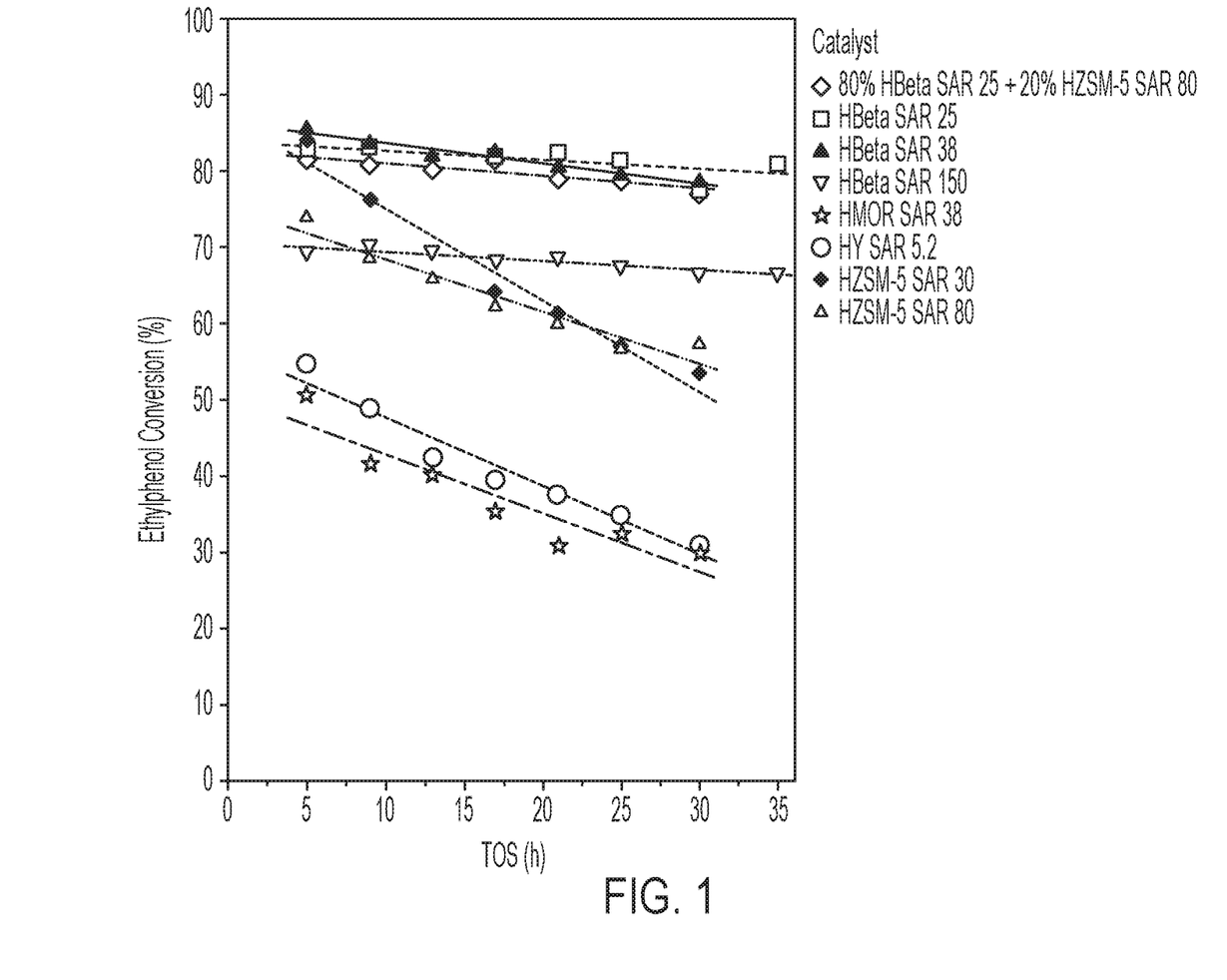
FIG. 1 illustrates a comparison of the conversion of 4-ethylphenol in a transalkylation process using a variety of catalysts comprising zeolites.

Table 2 and FIG. 1 show the results of the conversion of 4-ethylphenol. Conversion and selectivity were obtained after 30 h TOS (time on stream) for most runs. or 35 h TOS for HBeta SAR 25, HBeta SAR 150, and HZSM-5 SAR 80.

The product selectivity is based on the carbon product composition excluding toluene and 4-ethylphenol. BEX refers to benzene, ethylbenzene, and xylenes.

As shown in FIG. 1, the catalysts comprising HBeta SAR 25 and HBeta SAR 38 zeolites outperformed the catalysts comprising HZSM-5 SAR 30 and HZSM-5 SAR 80 zeolites. The catalyst comprising HBeta SAR 150 zeolite outperformed the HZSM-5 SAR 30 and HZSM-5 SAR 80 zeolites after 20 h TOS. In addition, the catalyst containing a combination of 80% HBeta SAR 25 zeolite and 20% HZSM-5 SAR 80 zeolite also outperformed the catalyst comprising HZSM-5 SAR 80 zeolite alone.

The catalyst comprising HBeta SAR 25 was the best catalyst for the reaction of 4-EP with toluene, with over 81% conversion and over 69% product selectivity to the desired phenol and ethyltoluene products. The catalyst comprising HBeta SAR 38 had the highest productivity to phenol+cresols at 1180 g/kg cat/hr and to phenol+cresols+alkylbenzenes (BEX and ethyltoluenes) at 3056 g/kg cat/hr.

The HBeta SAR 25 containing catalyst had only a 2% drop in conversion over 30 h TOS, demonstrating the stability of the catalyst.

Another desirable pathway (disproportionation of toluene) converts toluene to benzene, ethylbenzene and xylenes (BEX). The catalyst comprising HBeta SAR 25 had a 12.6% product selectivity for converting toluene to BEX.

A catalyst comprising a mixture of 80% HBeta SAR 25 with 20% HZSM-5 SAR 80 had a slightly lower conversion of about 77% compared to 81% for a catalyst comprising all HBeta SAR 25; however, the selectivity to the desired products (phenol+ethyltoluene) was improved from 69% to over 72%, while the amount of other products was decreased from 10.0% to 7.7%.

Example 2

Several commercial zeolites were evaluated for the transalkylation of 2,6 xylenol with toluene to form phenol, cresols, benzene, xylenes along with other alkylbenzenes. The reaction conditions included using an isothermal fixed bed reactor set to a temperature of 400° C., a pressure of 1350 psig, a WHSV of 2.3 $h^{-1}$, 1.25 g catalyst, toluene: feed of 10 mol/mol, and $N_2$ feed rate of 25 mL/min. The catalyst was pretreated in $N_2$ and heated to 200° C. (3° C./min) and held at 200° C. for 2 h followed by heating to 450° C. (5° C./min) and held for 3 h before cooling down to 400° C.

Conversion and selectivity were obtained at 35 h TOS.

Figure 2:
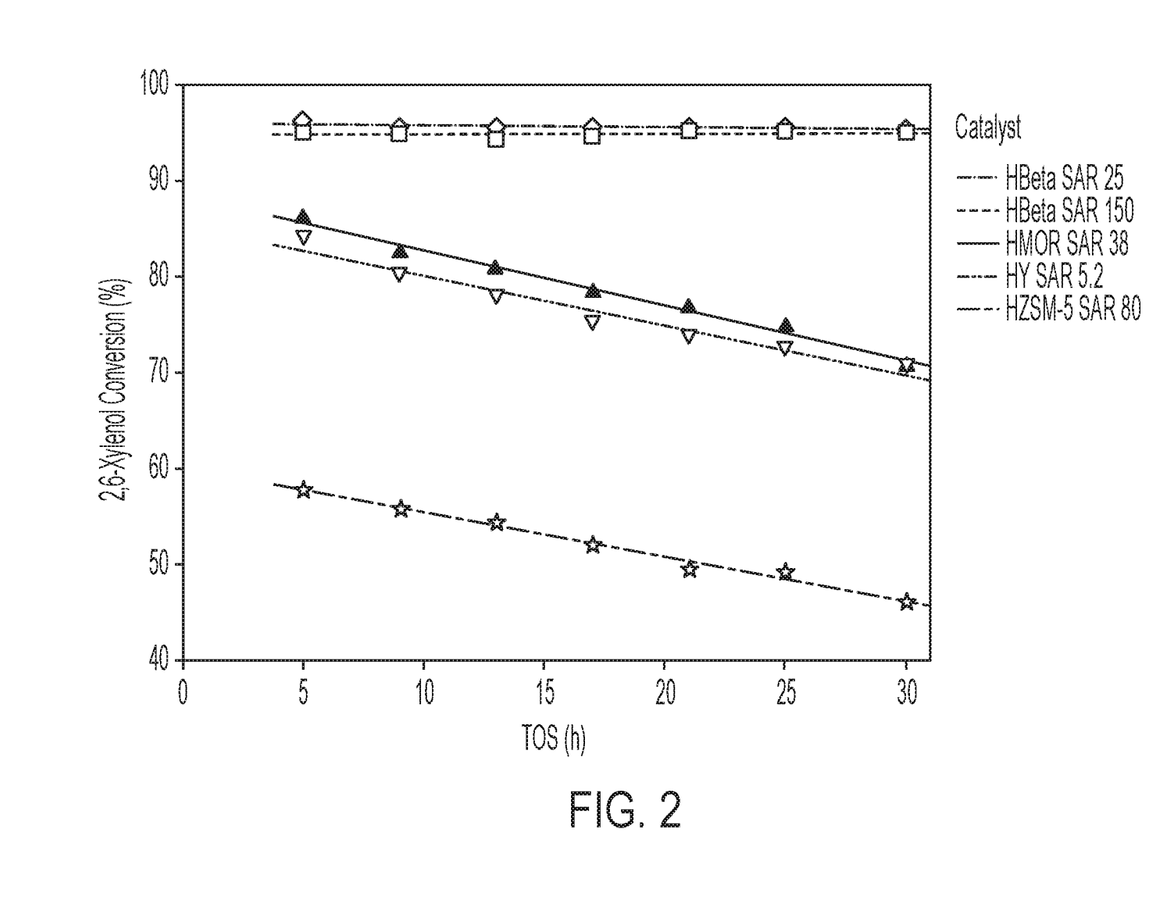
FIG. 2 illustrates a comparison of the conversion of 2,6-xylenols in a transalkylation process using a variety of catalysts comprising zeolites.

As shown in Table 3 and FIG. 2, the HBeta SAR 25 and HBeta SAR 150 zeolites outperformed the HZSM-5 SAR 80 zeolite.

HBeta SAR 150 was the best catalyst for this reaction as well, with over 95% conversion and over 55% selectivity to the desired cresols and xylenes products as shown in Table 2. The HBeta SAR 150 had the highest productivity to phenol+cresols at 931 g/kg cat/hr and to phenol+cresols+alkylbenzenes at 2791 g/kg cat/hr. Furthermore, there was only 1% drop in conversion over 25 h TOS. HBeta SAR 25 also performed nearly as well as HBeta SAR 150, with over 95% conversion and 52% selectivity to the desired cresols and xylenes products.

Although the 2,6-xylenol conversion was higher compared to 4-EP, the methyl group of the 2,6-xylenol was found to be harder to remove than the ethyl group of 4-EP. 4-EP transalkylation only showed 5.4% selectivity to isomerization products (other ethylphenols), while the xylenol transalkylation had a much higher selectivity to isomerization products (other xylenols) of 23.8% for HBeta SAR 25.

Example 3

Commercial zeolites were evaluated for the transalkylation of 4-ethylphenol (4-EP) with toluene to form phenol and ethyltoluenes. The conditions were the same as Example 1 except the gas feed was a mixture of $N_2$ at a feed rate of 12.5 mL/min and $H_2$ at a feed rate of 12.5 mL/min.

Conversion and selectivity were obtained at 30 h TOS.

Figure 3:
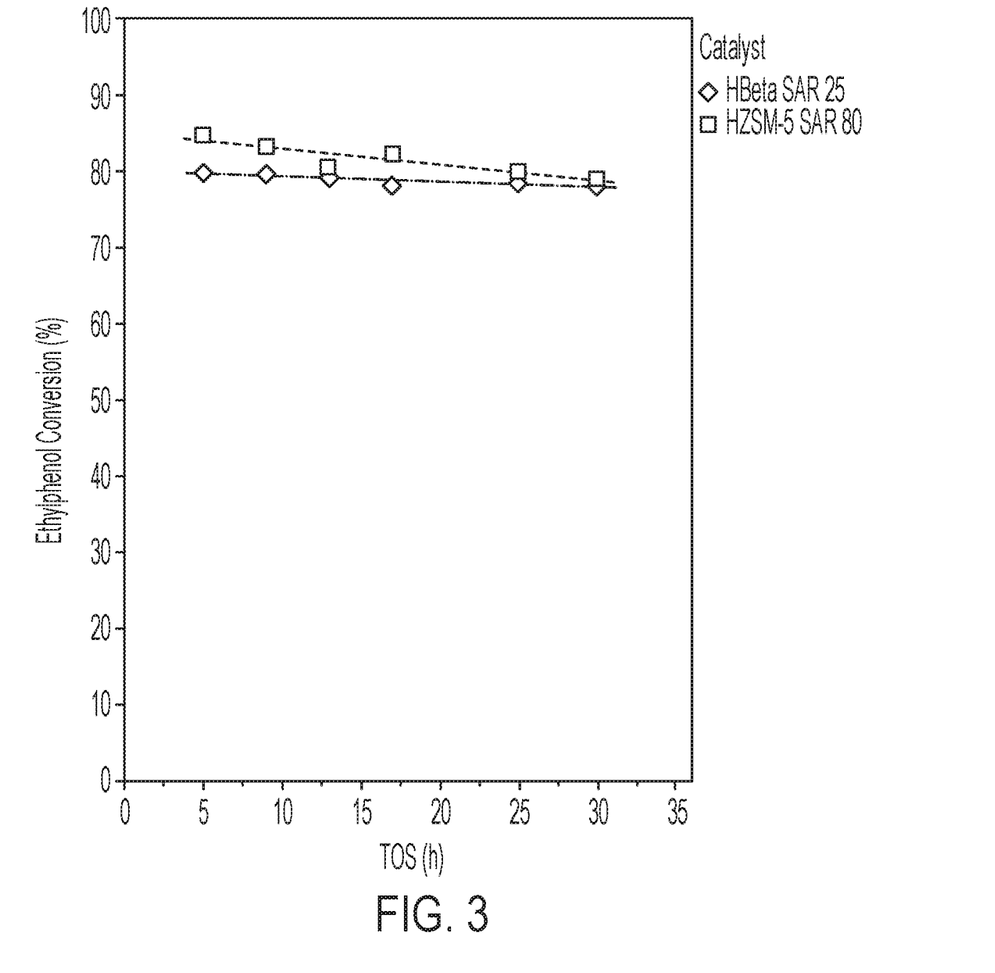
FIG. 3 illustrates a comparison of the conversion of 4-ethylphenol in a transalkylation process with $N_2$ and $H_2$ co-feed using HZSM-5 SAR 80 and HBeta SAR 25 zeolites.

As shown in Table 4 and FIG. 3, the addition of the $H_2$ co-feed increased the ethylphenol conversion of the HZSM-5 SAR 80 to 78.8% compared to 77.9% for the HBeta SAR 25. The phenol and cresol productivity was also higher at 1050 g/kg cat/hr, but the phenol+cresol+alkylbenzenes productivity of 2349 g/kg cat/hr was lower than for HBeta SAR 25 at 2387 g/kg cat/hr.

Example 4

Several commercial zeolites were evaluated for the transalkylation of cresylic acid (SASOL, CA68) with toluene to form phenol, cresols, ethyltoluene, xylenes, along with benzene and other alkylbenzenes. The cresylic acid composition was 25 wt % cresols, 34.5 wt % xylenols, 38.5 wt % ethylphenols, and 2.0 wt % other compounds (as measured). The reaction conditions included using an isothermal fixed bed reactor set to a temperature of 400° C., a pressure of 1350 psig, a WHSV of 2.3 $h^{-1}$, 1.25 g catalyst, toluene: cresylic acid of 8.2 g/g, $N_2$ feed rate of 12.5 mL/min, and $H_2$ feed rate of 12.5 mL/min. The catalyst was pretreated in $N_2$, heated to 200° C. (3° C./min), and held at 200° C. for 2 h, followed by heating to 450° C. (5° C./min) and holding for 3 h before cooling down to 400° C.

The conversion and selectivity were obtained at 30 h TOS except for HY SAR which were obtained at 25 h TOS. Negative selectivity means that cresols were destroyed in the process.

Figure 4A:
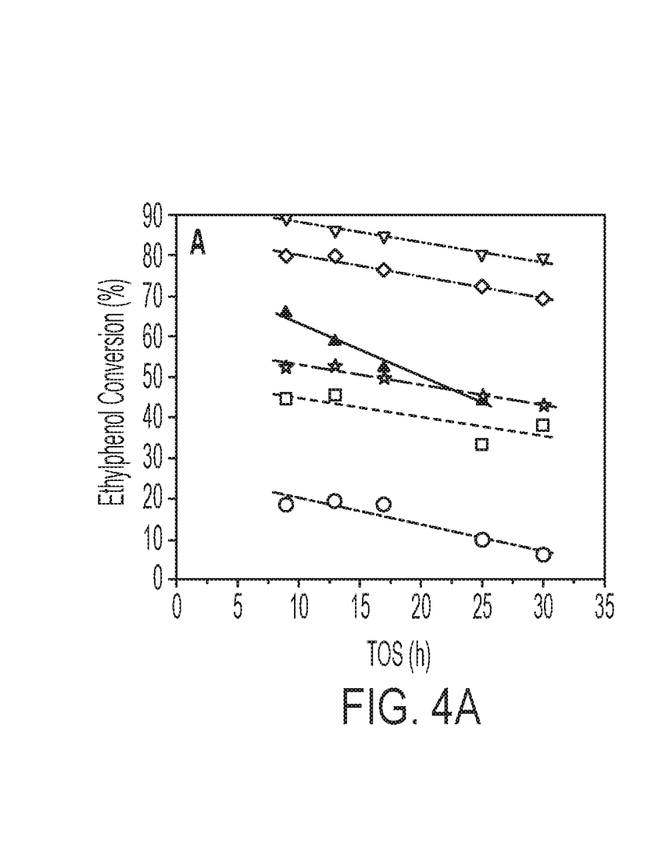
FIG. 4 illustrates a comparison of the conversion of (A) ethylphenols and (B) xylenols from a cresylic acid feed in a transalkylation process using a variety of catalysts comprising zeolites.
Figure 4B:
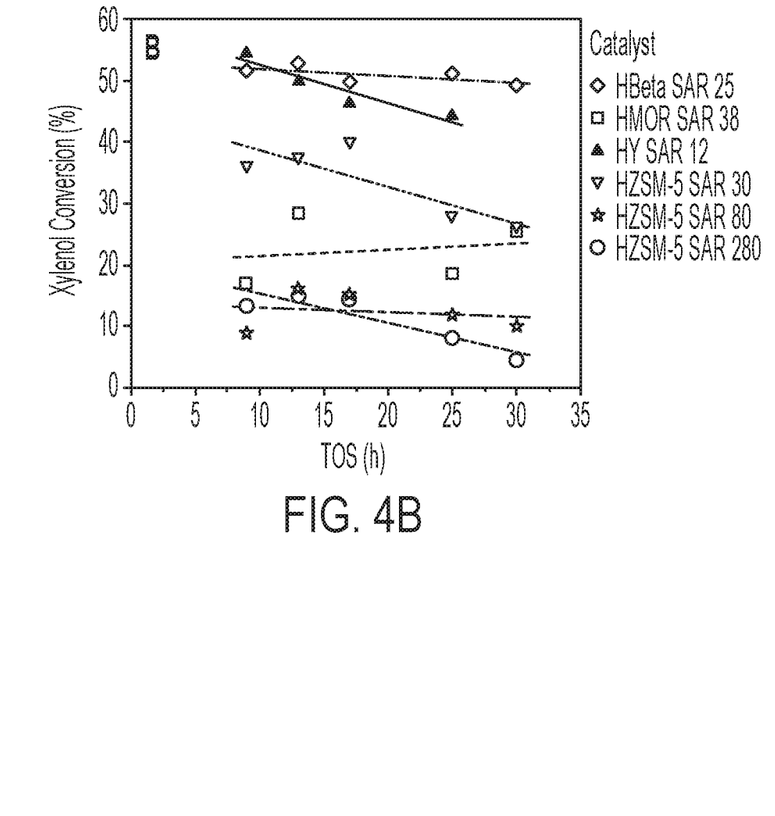

As shown in Table 5 and FIGS. 4A and 4B, HBeta SAR 25 was found to be good at converting both ethylphenol and xylenol in the cresylic acid compared to the other zeolites tested. HZSM-5 SAR 30 was found to be a better catalyst for ethylphenol conversion than HBeta SAR 25, with 79% conversion compared to 69% conversion for HBeta SAR 25. However, for xylenol conversion, HBeta SAR 25 was the better catalyst, with 49% conversion, compared with 26% conversion for HZSM-5 SAR 30. HZSM-5 SAR 30 was found to have the highest phenol+cresol productivity at 472 g/kg cat/hr slightly higher than HBeta SAR 25 at 468 g/kg cat/hr. However, HBeta SAR 25 had the highest productivity to phenol+cresols+alkylbenzenes at 1235 g/kg cat/hr.

All of the catalysts had greater than 90% selectivity to desired products (phenol, cresols, ethyltoluenes, and BEX) with less than 10% selectivity to other products (diethylphenols, gases, and unknown liquids).

Figure 5A:
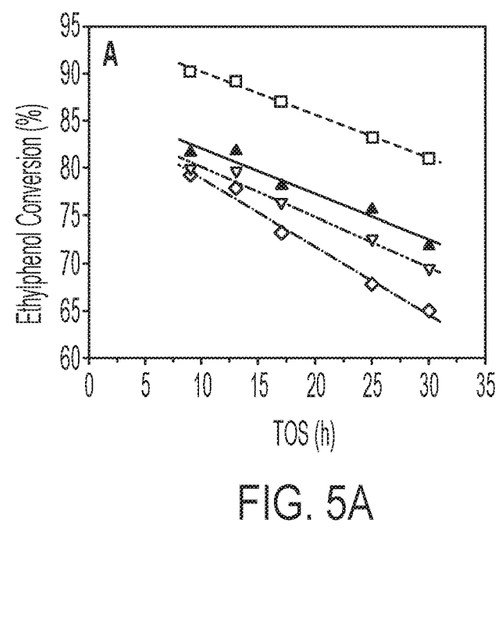
FIG. 5 illustrates a comparison of the conversion of (A) ethylphenols and (B) xylenols from a cresylic acid feed in a transalkylation process using HBeta SAR 25 compared to HBeta SAR 25 (80%) mixed with other zeolites (20%).
Figure 5B:
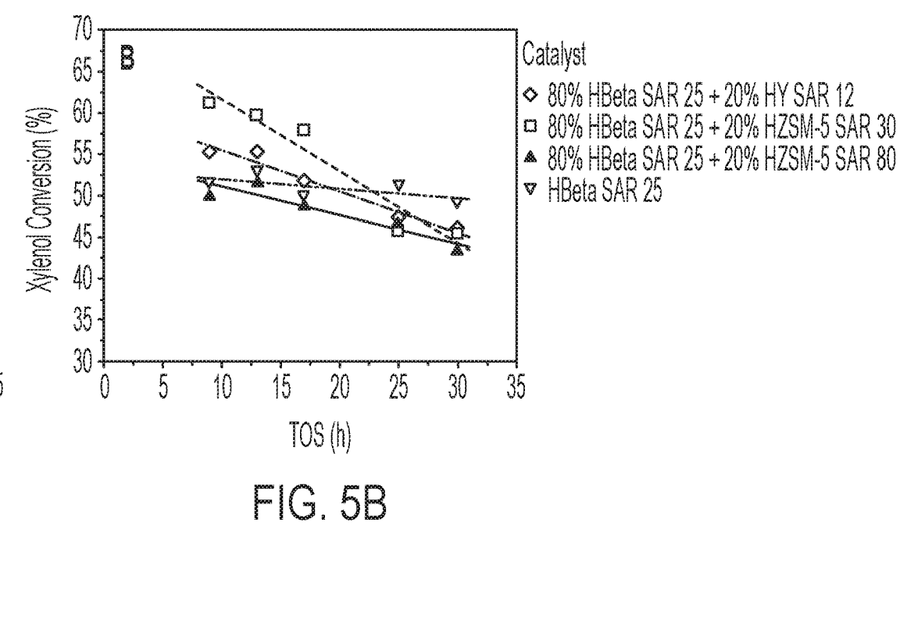

HBeta SAR 25 (80%) was then mixed with several other catalysts (20%) and the results are shown in FIGS. 5A and 5B. The addition of 20% HZSM-5 SAR 30 increased the ethylphenol conversion to 81%, while the xylenol conversion was slightly lower than the pure HBeta SAR 25 at 45.5% conversion. The amount of unknown liquids was also decreased to 3.0%, compared to 5.3% on the pure HBeta SAR 25. This catalyst mixture was also found to have the highest phenol+cresol productivity at 509 g/kg cat/hr and phenol+cresols+alkylbenzenes productivity at 1368 g/kg cat/hr.

TABLE 1

| Zeolite | IZA Code | Pore Diameter | Ring size | Pore Structure |
|---|---|---|---|---|
| Y | FAU | 7.4 × 7.4 | 12 | 3D |
| Beta | BEA | 6.6 × 6.7 | 12 | 3D |
|  |  | 5.6 × 5.6 | 12 |  |
| Mordenite | MOR | 6.5 × 7.0 | 12 | 1D |
|  |  | 3.4 × 4.8 | 8 |  |
|  |  | 2.6 × 5.7 | 8 |  |
| ZSM-5 | MFI | 5.3 × 5.6 | 10 | 3D |
|  |  | 5.1 × 5.5 | 10 |  |
| Ferrierite | FER | 4.2 × 5.4 | 10 | 2D |
|  |  | 3.5 × 4.8 | 8 |  |

TABLE 2

| Catalyst | 4EP Conv. (%) | Phenol (%) | Ethyl toluenes (%) | BEX (%) | Methyl phenols (%) |
|---|---|---|---|---|---|
| HZSM-5 SAR 30 | 53.5 | 33.5 | 28.8 | 3.8 | 1.6 |
| HZSM-5 SAR 80 | 57.4 | 36.0 | 31.5 | 4.6 | 0.5 |
| HBeta SAR 25 | 81.0 | 34.4 | 34.5 | 12.6 | 3.1 |
| HBeta SAR 38 | 78.6 | 31.3 | 32.6 | 15.9 | 4.3 |
| HBeta SAR 150 | 66.5 | 28.0 | 28.2 | 16.9 | 1.7 |
| HY SAR 5.2 | 31.0 | 39.7 | 20.2 | 3.6 | 0.7 |
| HMOR SAR 38 | 30.0 | 29.6 | 18.4 | 7.2 | 0.0 |
| 80% HBeta SAR 25 + 20% HZSM-5 SAR 80 | 76.9 | 36.8 | 35.6 | 10.1 | 1.8 |

| Catalyst | Other Ethyl phenols (%) | Others (%) | Phenol + Cresols (g/kg cat/h) | Phenol + Cresols + Alkylbenzenes (g/kg cat/h) |
|---|---|---|---|---|
| HZSM-5 SAR 30 | 25.5 | 6.8 | 495 | 1073 |
| HZSM-5 SAR 80 | 22.7 | 4.7 | 591 | 1308 |

TABLE 2-continued

| HBeta SAR 25 | 5.4 | 10.0 | 968 | 2439 |
| HBeta SAR 38 | 5.3 | 10.7 | 1180 | 3056 |
| HBeta SAR 150 | 11.4 | 13.8 | 618 | 1712 |
| HY SAR 5.2 | 11.4 | 24.4 | 365 | 631 |
| HMOR SAR 38 | 31.9 | 12.9 | 216 | 433 |
| 80% HBeta SAR 25 + 20% HZSM-5 SAR 80 | 8.0 | 7.7 | 969 | 2354 |

TABLE 3

| Catalyst | 2, 6 Xyl Conv. (%) | Phenol (%) | Cresols (%) | Other Xylenols (%) | Benzene (%) |
|---|---|---|---|---|---|
| HZSM-5 SAR 80 | 46.2 | 4.0 | 2.1 | 72.3 | 8.0 |
| HBeta SAR 25 | 95.4 | 5.7 | 19.1 | 23.8 | 9.7 |
| HY SAR 5.2 | 70.7 | 2.5 | 13.9 | 57.3 | 5 |
| HBeta SAR 150 | 95.0 | 4.0 | 19.7 | 19.3 | 13.6 |
| HMOR SAR 38 | 70.8 | 0.0 | 8.1 | 82.2 | 1.2 |

| Catalyst | Xylenes (%) | Other Alkyl benzenes (%) | Others (%) | Phenol + Cresols (g/kg cat/h) | Phenol + Cresols + Alkyl benzenes (g/kg cat/h) |
|---|---|---|---|---|---|
| HZSM-5 SAR 80 | 7.1 | 3.4 | 3.2 | 66 | 262 |
| HBeta SAR 25 | 33.0 | 1.0 | 7.7 | 825 | 2212 |
| HY SAR 5.2 | 10.7 | 0.0 | 10.7 | 297 | 558 |
| HBeta SAR 150 | 36.2 | 1.0 | 6.3 | 931 | 2791 |
| HMOR SAR 38 | 4.6 | 0.0 | 3.8 | 131 | 218 |

TABLE 4

| Catalyst | 4EP Conv. (%) | Phenol (%) | Ethyl toluenes (%) | BEX (%) | Methyl phenols (%) | Other Ethyl phenols (%) | Others (%) | Phenol + Cresols (g/kg cat/h) | Phenol + Cresols + Alkylbenzenes (g/kg cat/h) |
|---|---|---|---|---|---|---|---|---|---|
| HZSM-5 SAR 80 | 78.8 | 39.8 | 37.8 | 3.7 | 7.1 | 9.6 | 2.0 | 1050 | 2349 |
| HBeta SAR 25 | 77.9 | 35.7 | 34.8 | 11.1 | 4.5 | 7.1 | 7.8 | 1019 | 2387 |

TABLE 5

| Catalyst | EP Conv. (%) | Xyl. Conv. (%) | Phenol (%) | Cresols (%) | Ethyltoluenes (%) | BEX (%) | Others (%) | Phenol + Cresols (g/kg cat/h) | Phenol + Cresols + Alkylbenzenes (g/kg cat/h) |
|---|---|---|---|---|---|---|---|---|---|
| HZSM-5 SAR 30 | 79.0 | 26.0 | 42.9 | 2.0 | 39.2 | 13.5 | 2.4 | 472 | 1138 |
| HZSM-5 SAR 80 | 42.7 | 10.0 | 45.6 | −1.0 | 37.8 | 15.6 | 1.9 | 249 | 611 |
| HZSM-5 SAR 280 | 6.1 | 4.5 | 44.5 | 19.4 | 28.4 | 7.1 | 0.6 | 164 | 273 |
| HBeta SAR 25) | 69.3 | 49.1 | 33.3 | 5.1 | 22.7 | 33.6 | 5.3 | 468 | 1235 |
| HMOR SAR 38 | 38.2 | 25.6 | 37.8 | −1.1 | 23.4 | 33.5 | 6.4 | 169 | 463 |
| HY SAR 12 | 44.7 | 44.2 | 36.6 | −3.7 | 22.3 | 34.5 | 10.6 | 224 | 668 |
| 80% HBeta SAR 25 + 20% HZSM-5 SAR 30 | 81.0 | 45.5 | 34.0 | 4.9 | 28.2 | 29.9 | 3.0 | 509 | 1368 |
| 80% HBeta SAR 25 + 20% HZSM-5 SAR 80 | 71.9 | 43.4 | 35.0 | 4.2 | 26.6 | 30.9 | 3.3 | 421 | 1123 |
| 80% HBeta SAR 25 + 20% HY SAR 12 | 65.0 | 46.0 | 31.5 | 7.1 | 20.8 | 33.7 | 6.9 | 495 | 1265 |

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "about," means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for transalkylation comprising:
   transalkylating a coal-derived liquid stream comprising alkylphenols in a transalkylation reaction zone under transalkylation conditions in the presence of a co-reactant and a transalkylation catalyst comprising about 50% or more HBeta zeolite and 1 to 40% HZSM-5 zeolite to produce a transalkylation effluent stream comprising one or more of phenol, cresols, and alkylbenzenes, the process having increased conversion of alkylphenols to phenol, cresols, and alkylbenzenes compared to a catalyst consisting of HZSM-5 zeolite.

2. The process according to claim 1 wherein the silica/metal oxide molar ratio of the zeolite is 80 or below.

3. The process according claim 1 wherein aluminum in a framework structure of the zeolite is substituted by at least one of Fe, Ga, B, Ti, Sn, Zr, and combinations thereof.

4. The process of claim 1 wherein the zeolite further comprises a promoter comprising one or more of: transition metals, alkali metals, alkaline earth metals and rare earth metals, metal oxides, metal sulfides, metal nitrides, metal phosphides, and combinations thereof.

5. The process of claim 1 wherein the catalyst further comprises a support comprising alumina, silica, zirconia, titania, or combinations thereof.

6. The process of claim 1 wherein the coal-derived liquid stream comprises a mixture of alkylphenols comprising two or more of a methylphenol, an ethylphenol, a dimethylphenol, a butylphenol, a methylethylphenol, an indanol, and a naphthol, and optionally further comprising a propylphenol.

7. The process of claim 1 wherein the co-reactant comprises benzene, toluene, or a combination thereof.

8. The process of claim 1 wherein transalkylating the coal-derived liquid stream takes place in the presence of hydrogen, nitrogen, or a combination thereof.

9. The process of claim 1 wherein the transalkylation reaction zone comprises a fixed bed reactor, a moving bed reactor, an ebullated bed reactor, a fluidized bed reactor, a continuous catalyst regeneration (CCR) reactor, a semi-regenerative reactor, a batch reactor, a continuous stirred tank (CSTR) reactor, a slurry reactor, or combinations thereof.

10. The process of claim 1 wherein selectivity to phenol, cresols and alkylbenzenes is about 70% or more.

11. The process of claim 1 wherein the coal-derived liquid stream comprises a portion of a coal-derived feed stream comprising a low temperature coal tar stream, a medium temperature coal tar stream, a high temperature coal tar stream, a cresylic acid stream, or a crude phenolic mixture.

12. The process of claim 1 further comprising:
separating the transalkylation effluent into a phenol product stream comprising the phenol and an alkylbenzene stream comprising the alkylbenzenes.

13. The process of claim 12 further comprising:
separating the alkylbenzene stream into at least a recycle co-reactant stream comprising one or more of benzene or toluene; and
recycling the recycle co-reactant stream to the transalkylation zone and wherein the recycle co-reactant stream comprises at least a part of the co-reactant.

14. The process of claim 13 wherein separating the alkylbenzene stream into at least the recycle co-reactant stream comprises separating the alkylbenzene stream into at least the recycle co-reactant stream and a mixed xylenes stream comprising para-xylene, ortho-xylene, and meta-xylene; and
recovering one or more of para-xylene, ortho-xylene, or meta-xylene from the mixed xylenes stream.

15. The process of claim 12 wherein separating the transalkylation effluent into the phenol product stream and the alkylbenzene stream comprises separating the transalkylation effluent into the phenol product stream, the alkylbenzene stream, and a cresol product stream comprising the cresols, and further comprising:
recovering the cresol product stream.

16. The process of claim 1 wherein the transalkylation effluent stream further comprises unreacted alkylphenols, and wherein separating the transalkylation effluent into the product stream and the alkylbenzene stream comprises separating the transalkylation effluent into the phenol product stream, the alkylbenzene stream, and an unreacted alkylphenol stream comprising the unreacted alkylphenols, and further comprising:
recycling the unreacted alkylphenol stream to the transalkylation reaction zone.

17. The process of claim 1 further comprising:
providing a coal-derived feed stream comprising phenol and the coal-derived liquid stream;
separating the coal-derived feed stream into at least a phenol stream comprising phenol and the coal-derived liquid stream before transalkylating the coal-derived liquid stream; and
recovering the phenol stream.

18. The process of claim 1 further comprising:
providing a coal-derived feed stream comprising phenol and the coal-derived liquid stream;
separating the coal-derived feed stream into at least a phenol-cresol stream comprising phenol and cresols and the coal-derived liquid stream before transalkylating the coal-derived liquid stream; and
recovering the phenol-cresol stream.

* * * * *